United States Patent
Rutman

(10) Patent No.: US 6,582,410 B1
(45) Date of Patent: Jun. 24, 2003

(54) OSTOMY DRAINAGE APPARATUS

(76) Inventor: Will Rutman, 201 S. 2nd Ave., #27, Highland Park, NJ (US) 08904

(*) Notice: Subject to any disclaimer, the term of this patent is extended or adjusted under 35 U.S.C. 154(b) by 242 days.

(21) Appl. No.: 09/591,055

(22) Filed: Jun. 9, 2000

(51) Int. Cl.⁷ .................................................. A61F 5/44
(52) U.S. Cl. ....................................... 604/335; 604/332
(58) Field of Search ............................... 604/334, 335, 604/339, 332, 340, 333; 222/188

(56) References Cited

U.S. PATENT DOCUMENTS

| | | | |
|---|---|---|---|
| 3,039,464 A | | 6/1962 | Galindo |
| 3,385,298 A | * | 5/1968 | Fenton ......................... 604/332 |
| 3,415,299 A | * | 12/1968 | Hinman, Jr. et al. ......... 137/216 |
| 3,780,739 A | | 12/1973 | Frank |
| 3,841,332 A | * | 10/1974 | Treacle ................. 128/DIG. 24 |
| 3,881,486 A | * | 5/1975 | Fenton ......................... 604/335 |
| 4,266,765 A | * | 5/1981 | Sandoval et al. ....... 280/47.371 |
| 4,280,498 A | | 7/1981 | Jensen |
| 4,411,659 A | * | 10/1983 | Jensen et al. ................ 604/332 |
| 4,610,676 A | * | 9/1986 | Schneider et al. ........... 604/339 |
| 4,810,250 A | | 3/1989 | Wllenberg et al. |
| 5,429,626 A | * | 7/1995 | Fenton ......................... 604/339 |
| 5,935,115 A | * | 8/1999 | Espina ......................... 604/276 |
| 6,186,990 B1 | * | 2/2001 | Chen et al. ...................... 4/451 |

FOREIGN PATENT DOCUMENTS

WO    WO 93/17642    * 9/1993

* cited by examiner

Primary Examiner—Weilun Lo
Assistant Examiner—Linh Truong

(57) ABSTRACT

A ostomy drainage apparatus for increasing the amount of time between emptying cycles of an ostomy device. The ostomy drainage apparatus includes a container including an apex having a first opening. A lip extends upwardly away from the opening. A tubular member has an open first end and an open second end. The tubular member is generally hollow and is flexible. The first end is removably coupled to the lip of the container. A stoma engaging device removably engages the stoma of a user. A front wall has an aperture, and is removably coupled to the stoma engaging device such that fluid from the stoma may enter the ostomy bag through the aperture. The peripheral wall has a hole therein. A neck extends away from the hole. The second end of the tubular member may be removably coupled to the neck.

12 Claims, 5 Drawing Sheets

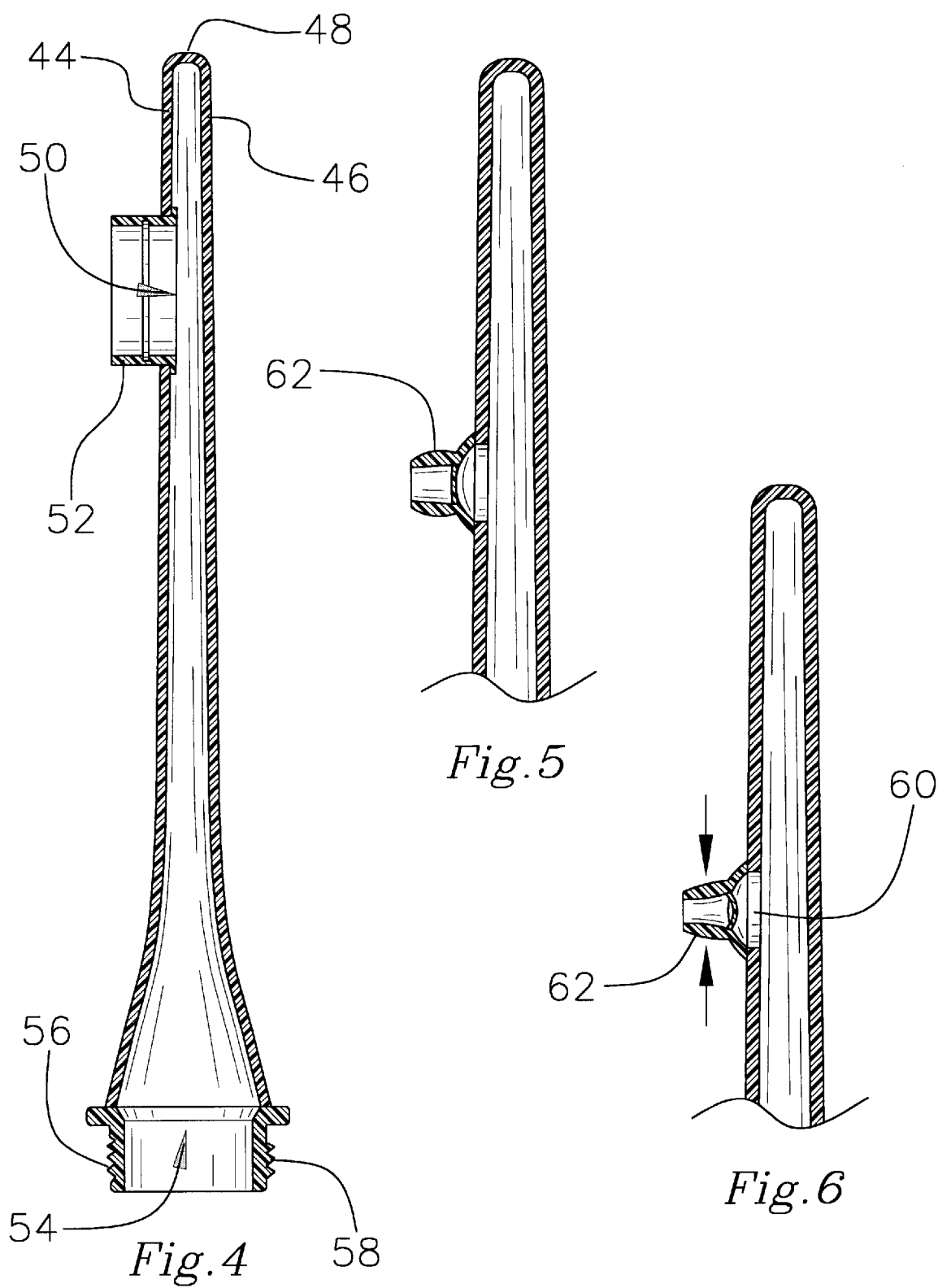

OSTOMY DRAINAGE APPARATUS

BACKGROUND OF THE INVENTION

1. Field of the Invention

The present invention relates to ostomy devices and more particularly pertains to a new ostomy drainage apparatus for increasing the amount of time between emptying cycles of an ostomy device.

2. Description of the Prior Art

The use of ostomy devices is known in the prior art. More specifically, ostomy devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,280,498; 4,411,659; 4,810,250; U.S. Des. Pat. No. 354,560; U.S. Pat. Nos. 3,780,560; and 3,039,464.

While these devices fulfill their respective, particular objectives and requirements, the aforementioned patents do not disclose a new ostomy drainage apparatus. The inventive device includes a container. The container has an apex having a first opening therein. A lip extends upwardly away from the opening. A tubular member is elongate and has an open first end and an open second end. The tubular member is generally hollow and is flexible. The first end is removably coupled to the lip of the container. A stoma engaging device removably engages the stoma of a user. An ostomy bag has a front wall, a back wall and a peripheral wall extends between and is integrally coupled to the front and back walls. The front wall has an aperture therein. The front wall is adapted to removably couple to the stoma engaging device such that fluid from the stoma may enter the ostomy bag through the aperture. The peripheral wall has a hole therein. A neck extends away from the hole. The second end of the tubular member may be removably coupled to the neck.

In these respects, the ostomy drainage apparatus according to the present invention substantially departs from the conventional concepts and designs of the prior art, and in so doing provides an apparatus primarily developed for the purpose of increasing the amount of time between emptying cycles of an ostomy device.

SUMMARY OF THE INVENTION

In view of the foregoing disadvantages inherent in the known types of ostomy devices now present in the prior art, the present invention provides a new ostomy drainage apparatus construction wherein the same can be utilized for increasing the amount of time between emptying cycles of an ostomy device.

The general purpose of the present invention, which will be described subsequently in greater detail, is to provide a new ostomy drainage apparatus apparatus and method which has many of the advantages of the ostomy devices mentioned heretofore and many novel features that result in a new ostomy drainage apparatus which is not anticipated, rendered obvious, suggested, or even implied by any of the prior art ostomy devices, either alone or in any combination thereof.

To attain this, the present invention generally comprises a container. The container has an apex having a first opening therein. A lip extends upwardly away from the opening. A tubular member is elongate and has an open first end and an open second end. The tubular member is generally hollow and is flexible. The first end is removably coupled to the lip of the container. A stoma engaging device removably engages the stoma of a user. An ostomy bag has a front wall, a back wall and a peripheral wall extends between and is integrally coupled to the front and back walls. The front wall has an aperture therein. The front wall is adapted to removably couple to the stoma engaging device such that fluid from the stoma may enter the ostomy bag through the aperture. The peripheral wall has a hole therein. A neck extends away from the hole. The second end of the tubular member may be removably coupled to the neck.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new ostomy drainage apparatus apparatus and method which has many of the advantages of the ostomy devices mentioned heretofore and many novel features that result in a new ostomy drainage apparatus which is not anticipated, rendered obvious, suggested, or even implied by any of the prior art ostomy devices, either alone or in any combination thereof.

It is another object of the present invention to provide a new ostomy drainage apparatus which may be easily and efficiently manufactured and marketed.

It is a further object of the present invention to provide a new ostomy drainage apparatus which is of a durable and reliable construction.

An even further object of the present invention is to provide a new ostomy drainage apparatus which is susceptible of a low cost of manufacture with regard to both materials and labor, and which accordingly is then susceptible of low prices of sale to the consuming public, thereby making such ostomy drainage apparatus economically available to the buying public.

Still yet another object of the present invention is to provide a new ostomy drainage apparatus which provides in the apparatuses and methods of the prior art some of the advantages thereof, while simultaneously overcoming some of the disadvantages normally associated therewith.

Still another object of the present invention is to provide a new ostomy drainage apparatus for increasing the amount of time between emptying cycles of an ostomy device.

Yet another object of the present invention is to provide a new ostomy drainage apparatus which includes a container. The container has an apex having a first opening therein. A lip extends upwardly away from the opening. A tubular member is elongate and has an open first end and an open second end. The tubular member is generally hollow and is flexible. The first end is removably coupled to the lip of the container. A stoma engaging device removably engages the stoma of a user. An ostomy bag has a front wall, a back wall and a peripheral wall extends between and is integrally coupled to the front and back walls. The front wall has an aperture therein. The front wall is adapted to removably couple to the stoma engaging device such that fluid from the stoma may enter the ostomy bag through the aperture. The peripheral wall has a hole therein. A neck extends away from the hole. The second end of the tubular member may be removably coupled to the neck.

Still yet another object of the present invention is to provide a new ostomy drainage apparatus that allows the user to sleep through an entire night without fear of spillage in the bed or overfilling of a traditional ostomy bag.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is a schematic cross-sectional view taken along line 4—4 of the present invention.

FIG. 5 is a schematic cross-sectional view taken along line 5—5 of the present invention.

FIG. 6 is a schematic cross-sectional view of the present invention.

DESCRIPTION OF THE PREFERRED EMBODIMENT

Figure 1:
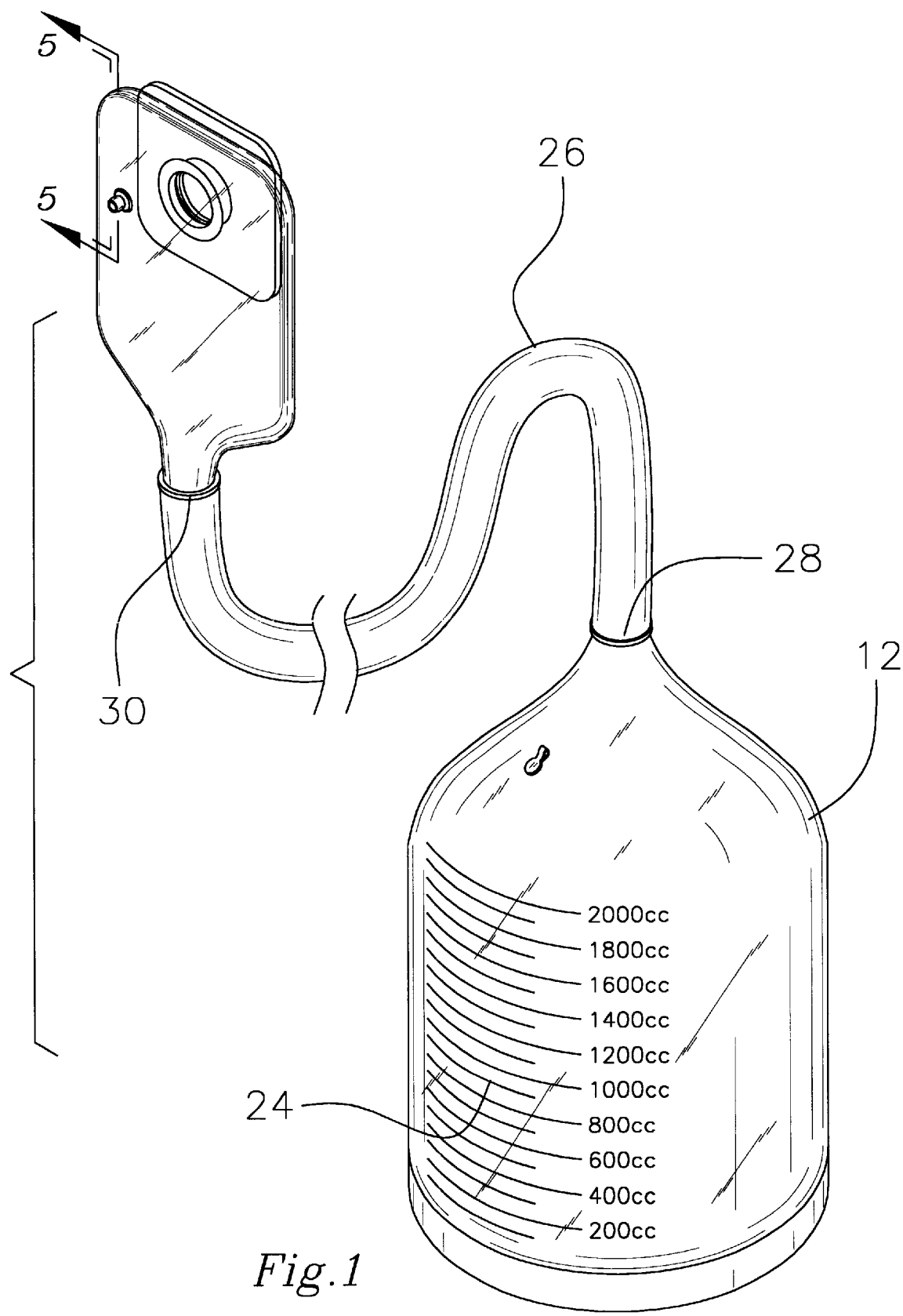
FIG. 1 is a schematic perspective view of a new ostomy drainage apparatus according to the present invention.
Figure 2:
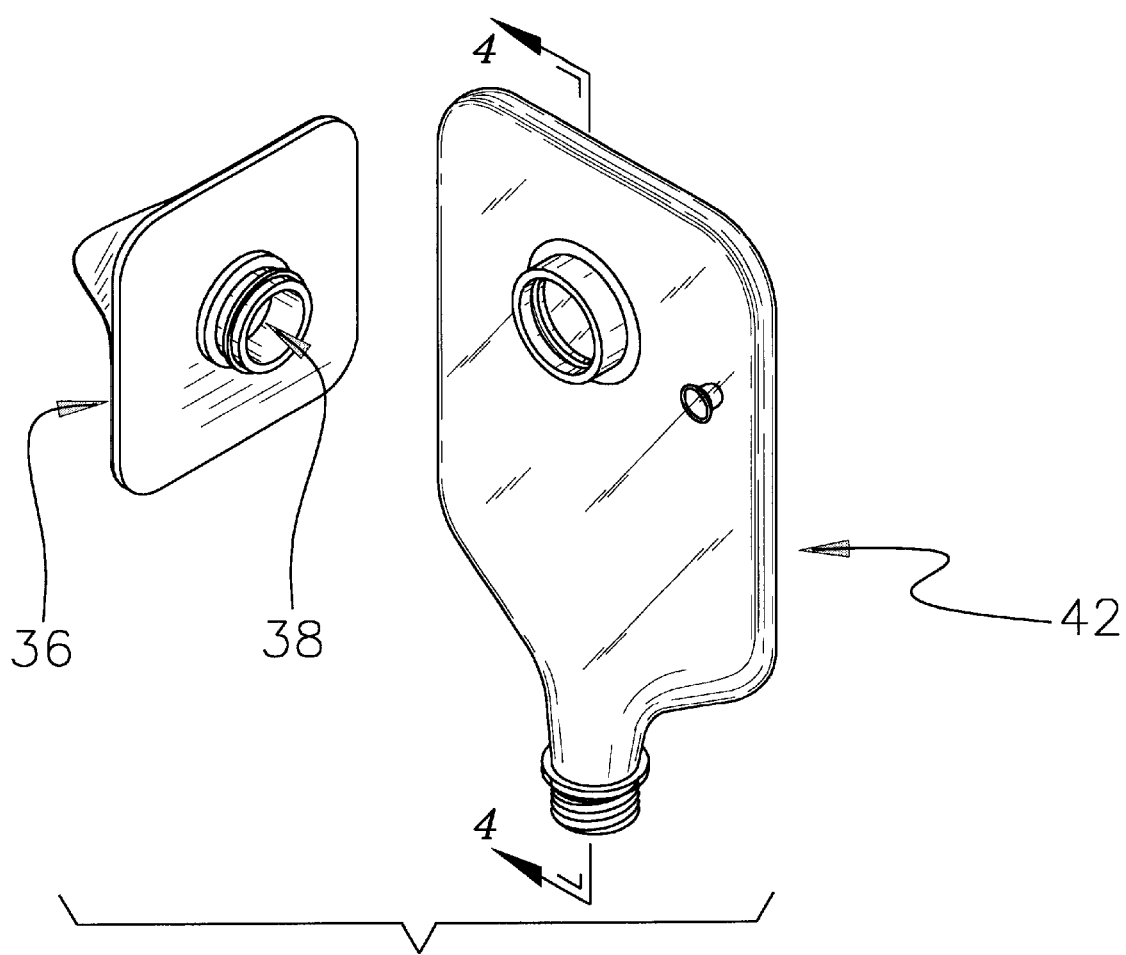
FIG. 2 is a schematic perspective view of the ostomy bag and stoma engaging device of the present invention.
Figure 3:
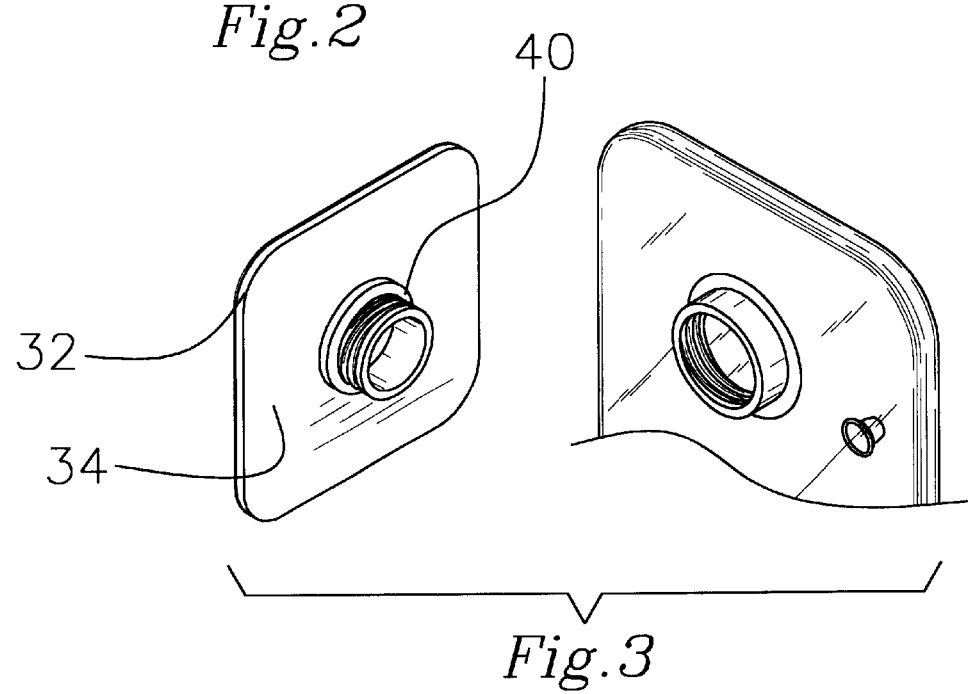
FIG. 3 is a schematic a perspective view of the ostomy bag and stoma engaging device of the present invention.
Figure 7:
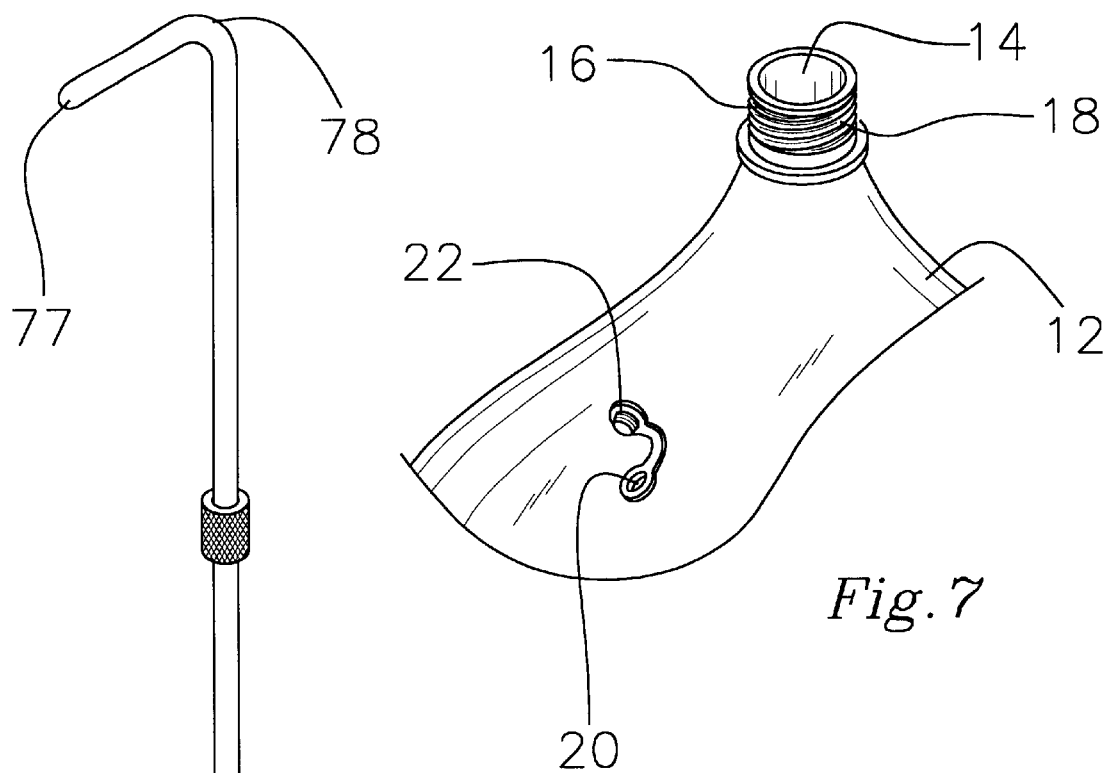
FIG. 7 is a schematic perspective view of the top side of the container of the present invention.
Figure 8:
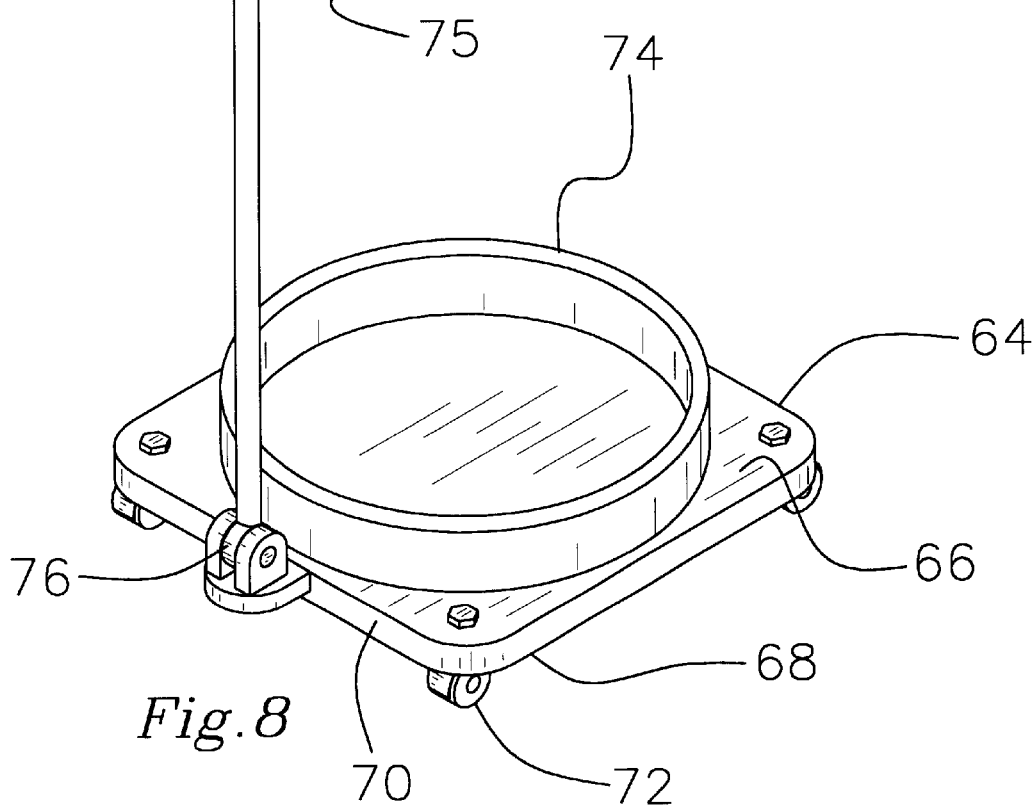
FIG. 8 is a schematic perspective view of the transporting means of the present invention.
Figure 9:
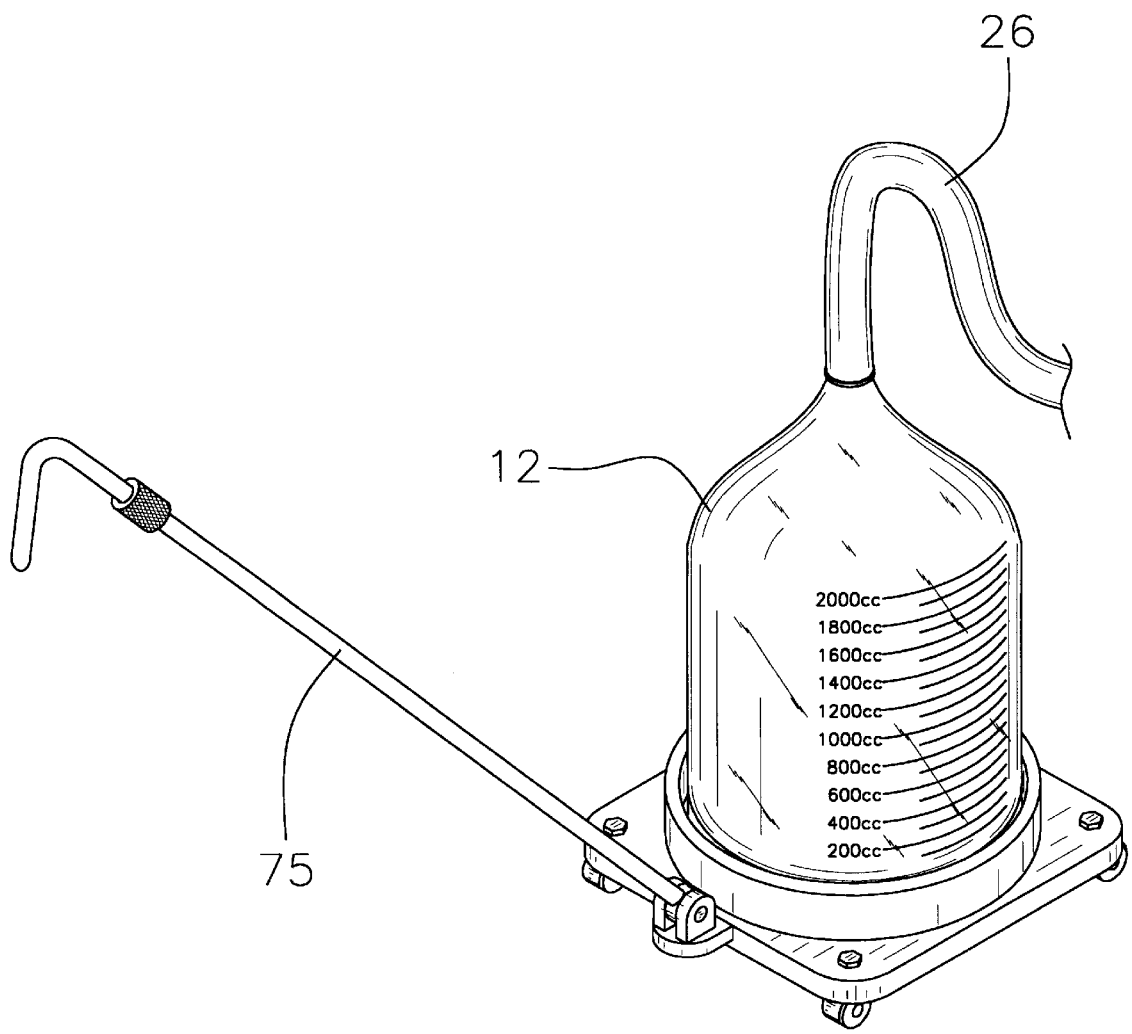
FIG. 9 is a schematic perspective view of the present invention.

With reference now to the drawings, and in particular to FIGS. 1 through 9 thereof, a new ostomy drainage apparatus embodying the principles and concepts of the present invention and generally designated by the reference numeral 10 will be described.

As best illustrated in FIGS. 1 through 9, the ostomy drainage apparatus 10 generally comprises a container 12. The container 12 has an apex having a first opening 14 therein. A lip 16 extends upwardly away from the opening 14. The lip 16 has outer threaded surface 18. The container 12 has a second opening 20 therein. The second opening 20 is in a top side of the container 12. A plug means 22 for plugging the second opening 20 is adapted for being removably inserted in the second opening 20. The container 12 is preferably translucent and may be transparent. The container 12 has an outer surface having indicia indicating volume calibrations 24 thereon. The container 12 has an inner volume greater than two liters.

A tubular member 26 is elongate and has an open first end 28 and an open second end 30. The tubular member 26 is generally hollow, and is flexible. The tubular member 26 preferably comprises an elastomeric material. The tubular member 26 has a diameter generally between 1 and 2 inches. The first end 28 is removably coupled to the lip 16 of the container 12. The tubular member 26 has a length greater than two feet.

A stoma engaging device comprises a panel 32 having a front side 34 and a back side 36. The back side 36 has an adhesive thereon for removably adhering to the body of the user. The panel 32 has an aperture 38 therein. The aperture 38 is located in a central area of the panel 32. A male collar 40 extends away from the aperture 38 and is integrally coupled to the front side 34 of the panel.

An ostomy bag 42 has a front wall 44, a back wall 46 and a peripheral wall 48 extending between and integrally coupled to the front 44 and back 46 walls. The front wall 44 has an aperture 50 therein. A female collar 52 extends away from the aperture 50 in the front wall 44 and is adapted to removably couple to the male collar 40. The peripheral wall has a hole 54 therein. A neck 56 extends away from the hole 54. The neck 56 has a threaded outer surface 58. The second end 30 of the tubular member 26 may be removably coupled to the neck 56. The neck 56 and the lip 16 are preferably threaded for greater integrity of the connection between them and the tubular member. The back wall 46 has an aperture 60 therein. A conventional valve 62 controls the opening of the aperture 60 in the back wall 46 and is integrally coupled to the back wall 46. The valve 62 comprises an air release valve. Applying pressure to opposite sides of the valve selectively actuates the valve.

A transporting means assists in the transporting of the container 12. The transporting means comprises a base wall 64. The base wall 64 has a top surface 66 and a bottom surface 68. The base wall has a perimeter edge 70. The bottom surface 68 has a plurality of wheels 72 rotatably coupled thereto. The top surface has an annular member 74 integrally coupled thereto and extending upwardly therefrom. The annular member 74 has an inner diameter substantially equal to an outer diameter of the container 12 such that the container 12 may be placed within the annular member 74. A handle member 75 comprising an elongate rod has a first end 76 and second end 77. The first end 76 is pivotally coupled to the perimeter edge 70 of the base wall 64. The rod has a bend 78 therein. The bend 78 is generally adjacent to the second end 77 such that a handler is defined between the second end 77 and the bend 78. The rod is a telescoping rod such a length of the rod may be selectively altered.

In use, the tubular member 26 is coupled to a generally conventional ostomy bag having a hole in the peripheral wall. The hole allows the ostomy bag 42 to drain into the container 12 which can safely hold large amounts of bodily fluids. This is needed for users at night and prevents the contents of a traditional ostomy bag from filling up in the middle of the night or from spilling onto the bed. The transporting means helps the user transport what could be a potentially heavy container once the container has a large amount of bodily fluids therein. The valve 62 in the ostomy bag 42 and the plug 22 in the container 12 may be opened to release gas which may build up therein.

As to a further discussion of the manner of usage and operation of the present invention, the same should be apparent from the above description. Accordingly, no further discussion relating to the manner of usage and operation will be provided.

With respect to the above description, then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An ostomy drainage assembly for removably coupling to a stoma in a user and retaining human waste fluid from the user, said assembly comprising:

a container, said container having an apex having a first opening therein, a lip extending upwardly away from said opening;

a tubular member, said tubular member being elongate and having an open first end and an open second end, said tubular member being generally hollow, said tubular member being flexible, said first end being removably coupled to said lip of said container;

a stoma engaging device for removably engaging the stoma of a user;

an ostomy bag, said ostomy bag having a front wall, a back wall and a peripheral wall extending between and integrally coupled to said front and back walls, said front wall having an aperture therein, said front wall being adapted to removably couple to said stoma engaging device such that fluid from the stoma may enter said aperture in said ostomy bag, said peripheral wall having a hole therein, a neck extending away from said hole, wherein said second end of said tubular member may be removably coupled to said neck; and said container having a second opening therein, said second opening being in a top side of said container, a plugging means for plugging said second opening, said plugging means being adapted for being removably inserted in said second opening.

2. The ostomy drainage assembly as in claim 1, wherein said container further comprises:

said container being generally translucent, said container having an outer surface having volume calibrations thereon, said container having an inner volume greater than two liters.

3. The ostomy drainage assembly as in claim 1, wherein said tubular member further comprises:

said tubular member preferably comprising an elastomeric material, said tubular member having a diameter generally between 1 and 2 inches, said tubular member having a length greater than two feet.

4. The ostomy drainage assembly as in claim 1, wherein said assembly comprises:

said stoma engaging device comprising a panel having a front side and a back side, said back side having an adhesive thereon for removably adhering to the body of the user, said panel having an aperture therein, said aperture being located in a central area of said panel, a male collar extending away from said aperture and integrally coupled to said front side of said panel; and said ostomy bag having a front wall, a back wall and a peripheral wall extending between and integrally coupled to said front and back walls, said front wall having an aperture therein, a female collar extending away from said aperture in said front wall, said female collar being adapted to removably couple to said male collar.

5. The ostomy drainage assembly as in claim 4, wherein said ostomy bag further comprises:

said back wall having an aperture therein, said aperture facilitating release of air from said container to limit pressurization, a valve for controlling the opening of said aperture in said back wall being integrally coupled to said back wall, said valve comprising an air release valve, wherein said valve may be selectively actuated by applying pressure to opposite sides of said valve.

6. An ostomy drainage assembly for removably coupling to a stoma in a user and retaining human waste fluid from the user, said assembly comprising:

a container, said container having an apex having a first opening therein, a lip extending upwardly away from said opening;

a tubular member, said tubular member being elongate and having an open first end and an open second end, said tubular member being generally hollow, said tubular member being flexible, said first end being removably coupled to said lip of said container;

a stoma engaging device for removably engaging the stoma of a user;

an ostomy bag, said ostomy bag having a front wall, a back wall and a peripheral wall extending between and integrally coupled to said front and back walls, said front wall having an aperture therein, said front wall being adapted to removably couple to said stoma engaging device such that fluid from the stoma may enter said aperture in said ostomy bag, said peripheral wall having a hole therein, a neck extending away from said hole, wherein said second end of said tubular member may be removably coupled to said neck; and a transporting means for transporting said container, said transporting means comprising a base wall, said base wall having an top surface and a bottom surface, said base wall having a perimeter edge, said bottom surface having a plurality of wheels rotatably coupled thereto, said top surface having an annular member integrally coupled thereto and extending upwardly therefrom, said annular member having an inner diameter substantially equal to an outer diameter of said container such that said container may be placed within said annular member, a handle member comprising an elongate rod, said rod having a first end and second end, said first end being coupled to said perimeter edge of said base wall.

7. An ostomy drainage assembly for removably coupling to a stoma in a user and retaining human waste fluid from the user, said assembly comprising:

a container, said container having an apex having a first opening therein, a lip extending upwardly away from said opening, said lip having outer threaded surface, said container having a second opening therein, said second opening, being in a top side of said container, a plug means for plugging said second opening, said plugging means being adapted for being removably inserted in said second opening said container being generally translucent, said container having an outer surface having volume calibrations thereon, said container having an inner volume greater than two liters;

a tubular member, said tubular member being elongate and having an open first end and an open second end, said tubular member being generally hollow, said tubular member being flexible, said tubular member comprising an elastomeric material, said tubular member having a diameter generally between 1 and 2 inches, said first end being removably coupled to said lip of said container, said tubular member having a length greater than two feet;

a stoma engaging device, said stoma engaging device comprising a panel having a front side and a back side, said back side having an adhesive thereon for removably adhering to the body of the user, said panel having an aperture therein, said aperture being located in a central area of said panel, a male collar extending away from said aperture and integrally coupled to said front side of said panel;

an ostomy bag, said ostomy bag having a front wall, a back wall and a peripheral wall extending between and integrally coupled to said front and back walls, said front wall having an aperture therein, a female collar extending away from said aperture in said front wall, said female collar being adapted to removably couple to said male collar, said peripheral wall having a hole therein, a neck extending away from said hole, said neck having a threaded outer surface, wherein said second end of said tubular member may be removably coupled to said neck, said back wall having an aperture therein, a valve for controlling the opening of said aperture in said back wall being integrally coupled to said back wall, said valve comprising an air release valve, wherein said valve may be selectively actuated by applying pressure to opposite sides of said valve;

a transporting means for transporting said container, said transporting means comprising a base wall, said base wall having an top surface and a bottom surface, said base wall having a perimeter edge, said bottom surface having a plurality of wheels rotatably coupled thereto, said top surface having an annular member integrally coupled thereto and extending upwardly therefrom, said annular member having an inner diameter substantially equal to an outer diameter of said container such that said container may be placed within said annular member, a handle member comprising an elongate rod, said rod having a first end and second end, said first end being pivotally coupled to said perimeter edge of said base wall, said rod having a bend therein, said bend being generally adjacent to said second end such that a handle is defined between said second end and said bend, said rod being a telescoping rod wherein a length of said rod may be selectively altered.

8. The ostomy drainage assembly as in claim 6, wherein said container further comprises:

said container having a second opening therein, said second opening being in a top side of said container, a plugging means for plugging said second opening, said plugging means being adapted for being removably inserted in said second opening.

9. The ostomy drainage assembly as in claim 6, wherein said container further comprises:

said container being generally translucent, said container having an outer surface having volume calibrations thereon, said container having an inner volume greater than two liters.

10. The ostomy drainage assembly as in claim 6, wherein said tubular member further comprises:

said tubular member preferably comprising an elastomeric material, said tubular member having a diameter generally between 1 and 2 inches, said tubular member having a length greater than two feet.

11. The ostomy drainage assembly as in claim 6, wherein said assembly comprises:

said stoma engaging device comprising a panel having a front side and a back side, said back side having an adhesive thereon for removably adhering to the body of the user, said panel having an aperture therein, said aperture being located in a central area of said panel, a male collar extending away from said aperture and integrally coupled to said front side of said panel; and said ostomy bag having a front wall, a back wall and a peripheral wall extending between and integrally coupled to said front and back walls, said front wall having an aperture therein, a female collar extending away from said aperture in said front wall, said female collar being adapted to removably couple to said male collar.

12. The ostomy drainage assembly as in claim 11, wherein said ostomy bag further comprises:

said back wall having an aperture therein, said aperture facilitating release of air from the container to limit pressurization, a valve for controlling the opening of said aperture in said back wall being integrally coupled to said back wall, said valve comprising an air release valve, wherein said valve may be selectively actuated by applying pressure to opposite sides of said valve.

* * * * *